United States Patent [19]
Burdick et al.

[11] Patent Number: 6,093,769
[45] Date of Patent: Jul. 25, 2000

[54] FLUIDIZED POLYMER SUSPENSIONS OF CATIONIC POLYSACCHARIDES IN POLYOLS AND USE THEREOF IN PERSONAL CARE COMPOSITIONS

[75] Inventors: Charles Lee Burdick, New Castle County, Del.; Mohand Melbouci; Hans Hofman, both of Dordrecht, Netherlands; Jacobus Johannes deBruin, Zwijnrdrecht, Netherlands

[73] Assignee: Hercules Incorporated, Wilmington, Del.

[21] Appl. No.: 08/974,189

[22] Filed: Nov. 19, 1997

[51] Int. Cl.[7] .............................. A61K 9/10; A61K 7/06; C08K 3/36
[52] U.S. Cl. .................... 524/767; 424/78.02; 424/70.13
[58] Field of Search .................. 514/781; 424/78.02, 424/78.03

[56] References Cited

U.S. PATENT DOCUMENTS

| | | | |
|---|---|---|---|
| 3,472,840 | 10/1969 | Stone et al. | 260/231 |
| 3,894,879 | 7/1975 | Colegrove | 106/189 |
| 3,894,880 | 7/1975 | Colegrove | 106/208 |
| 4,031,307 | 6/1977 | DeMartino et al. | 536/114 |
| 4,299,755 | 11/1981 | Keggenhoff et al. | 260/23 |
| 4,312,675 | 1/1982 | Pickens et al. | 106/171 |
| 4,325,861 | 4/1982 | Braun et al. | 523/205 |
| 4,374,216 | 2/1983 | Dammann | 524/35 |
| 4,453,979 | 6/1984 | DeMasi et al. | 106/188 |
| 4,566,977 | 1/1986 | Hatfield | 252/8.5 |
| 4,585,812 | 4/1986 | Field | 523/221 |
| 4,663,159 | 5/1987 | Brode, II et al. | 424/70 |
| 4,799,962 | 1/1989 | Ahmed | 106/188 |
| 5,037,930 | 8/1991 | Shih | 527/301 |
| 5,080,717 | 1/1992 | Young | 106/197.1 |
| 5,096,490 | 3/1992 | Burdick | 106/171 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,228,908 | 7/1993 | Burdick et al. | 106/194 |
| 5,228,909 | 7/1993 | Burdick et al. | 106/194 |
| 5,288,484 | 2/1994 | Tashjian | 424/70.13 |
| 5,362,312 | 11/1994 | Skaggs et al. | 106/189 |
| 5,387,675 | 2/1995 | Yeh | 536/18.7 |
| 5,473,059 | 12/1995 | Yeh | 536/18.7 |
| 5,487,777 | 1/1996 | Lundan et al. | 106/188 |

FOREIGN PATENT DOCUMENTS

| | | |
|---|---|---|
| 2565109 | 12/1985 | France . |
| 54-135234 | 10/1979 | Japan . |
| 60-221493 | 11/1985 | Japan . |
| 10 072340 | 3/1998 | Japan . |
| WO 97/46606 | 12/1997 | WIPO . |
| WO 97/493376 | 12/1997 | WIPO . |

*Primary Examiner*—Peter F. Kulkosky
*Attorney, Agent, or Firm*—Martin F. Sloan

[57] ABSTRACT

There are disclosed stable fluidized polymer suspensions containing cationic polysaccharide, stabilizing agent and water-soluble polyol. The preferred cationic polysaccharides are cationic guar and cationic hydroxypropyl guar. Processes for preparing personal care compositions utilizing the fluidized polymer suspensions are also disclosed. Using the fluidized polymer suspensions in the processes provides advantages of more rapid dissolution and avoidance of lumps and gels when compared to using dry, powdered cationic polysaccharides.

17 Claims, No Drawings

FLUIDIZED POLYMER SUSPENSIONS OF CATIONIC POLYSACCHARIDES IN POLYOLS AND USE THEREOF IN PERSONAL CARE COMPOSITIONS

FIELD OF THE INVENTION

This invention relates to fluidized polymer suspensions of cationic polysaccharides and their use in preparing personal care compositions, in particular, hair and skin care compositions.

BACKGROUND OF THE INVENTION

Cationic polysaccharides have been used in many personal care applications, e.g. shampoos, shower gels, hair styling compositions, skin creams and lotions, where they provide rheological properties to the compositions and desirable properties to the hair and skin.

In most cases cationic polysaccharides used in personal care compositions are utilized as dry powders. However, handling of powders is often accompanied by dusting which can be a cause of health and safety problems. Moreover, in the case of cationic polysaccharides the dusting problem is particularly troublesome, because the cationic material tends to adhere strongly to anionic surfaces. Furthermore, particulate polysaccharides are known to lump excessively when added to water, resulting in low rates of solution, and so special care must be taken when adding these materials to water to avoid lumping and gel formation. Often unacceptable gel levels remain in these solutions. For these reasons there has been a desire to develop cationic polysaccharide products that are readily dispersible in aqueous media by dispersing them in liquids with which they are immiscible but which are useful in particular personal care applications.

U.S. Pat. No. 4,799,962 to Ahmed discloses particulate water-soluble polymers dispersed in liquid medium comprised of low molecular weight polyethylene glycol, water and high molecular weight polyethylene glycol. Dispersion of cationic polysaccharides is not disclosed.

U.S. Pat. No. 5,487,777 to Lundan et al. relates to slurries of carboxymethyl cellulose comprising: a) 10 to 60% of carboxymethyl cellulose, b) 40 to 60% of water-soluble polyethylene glycol, the average molecular weight of which is below about 1,000, and c) 1 to 50% of an inert powder or dispersion.

U.S. Pat. No. 5,362,312 to Skaggs et al. discloses a polymeric fluid composition comprising: a) water-soluble polysaccharide, b) water-soluble polyethylene glycol or thickened polyethylene glycol, c) one or more viscosified polyol fluid components, and d) one or more viscosifying polysaccharides. The polysaccharides disclosed do not include cationic polysaccharides.

The solvation and solubility properties of various water-soluble polysaccharides can vary widely. Therefore, information on fluidized polymer suspensions of anionic and nonionic polysaccharides is of little utility in predicting what systems will be suitable for preparing fluidized polymer suspensions of cationic polysaccharides. For this reason, the fluidized polymer suspensions of cationic polysaccharides disclosed herein are novel in composition and in their use in preparing personal care compositions.

SUMMARY OF THE INVENTION

In one embodiment of the invention a fluidized polymer suspension comprises: a) cationic polysaccharide, b) stabilizing agent, and c) water-soluble polyol that is not a solvent for the cationic polysaccharide.

In another embodiment of the invention a process of preparing a personal care composition comprises: a) providing a fluidized polymer composition comprising i) cationic polysaccharide, ii) stabilizing agent, and iii) water-soluble polyol that is a non-solvent for the cationic polysaccharide; and b) mixing the fluidized polymer suspension with one or more personal care active ingredients.

DETAILED DESCRIPTION OF THE INVENTION

It is characteristic of the fluidized polymer suspensions of this invention that they are stable as made. By the term "stable as made" it is meant that the suspension does not immediately separate into two or more distinct layers when standing. In some instances, where the suspension will be used within a short period of time, it is sufficient that the suspensions be moderately stable, i.e., at least sufficiently stable so that the cationic polysaccharide remains dispersed or may be readily redispersed after standing for a short period of time, e.g. several hours or overnight. However, dispersed cationic polysaccharides tend to agglomerate upon settling into gels or solids which cannot readily be redispersed after standing for more than a few days (or in some cases much shorter periods of time). Therefore it is often preferred that the suspensions be storage stable over much longer periods of time since they will frequently be used in applications where they must be stored for periods of about one to six months. The fluidized polymer suspensions of this invention are stable as made, preferably stable for at least about one week, more preferably for at least about 8 weeks, and even more preferably for at least about 6 months.

Cationic polysaccharides for use in the invention include any naturally occurring cationic polysaccharide as well as polysaccharides and polysaccharide derivatives that have been cationized by chemical means, e.g. quaternization with various quaternary amine compounds containing reactive chloride or epoxide sites. Example of such cationic polysaccharides include, but are not restricted to, cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose. Preferred cationic polysaccharides for use in the invention are cationic guar and cationic hydroxypropyl guar.

Methods for preparation of the cationic polysaccharides are disclosed in U.S. Pat. Nos. 4,663,159; 5,037,930; 5,473,059; 5,387,675; 3,472,840 and 4,031,307, all of which are incorporated herein by reference in their entireties.

Polyols used for preparing the fluidized polymer suspension of the invention are water-soluble, essentially non-solvents for the cationic polysaccharides (i.e., the cationic polysaccharides are soluble at a level of no more than about 5%) and preferably liquids. Examples of such polyols include, but are not restricted to polyethylene glycol, propylene glycol, polypropylene glycol, diethylene glycol, glycerine and ethylene glycol. The preferred polyol is polyethylene glycol.

Polyethylene glycol, also called "polyoxyethylene", "poly (ethylene oxide)", or "polyglycol" is a well known condensation product of ethylene glycol having the formula $H(OCH_2CH_2-)_n-OH$. Polyethylene glycols are commercially available in several grades and molecular weights. Preferred polyethylene glycols for the invention have a relatively low molecular weight of between about 150 and 1,000. More preferably the molecular weight is from about 200 to about 700, and most preferably from about 250 to about 600.

In the fluidized polymer suspensions of the invention, the cationic polysaccharide is preferably from about 10 to about 65 wt. % and the polyol from about 35 to about 90 wt. % of the total weight of the fluidized polymer suspension. More preferably the cationic polysaccharide is from about 15 to about 60 wt. % and the polyol from about 40 to about 85 wt. %. Most preferably the cationic polysaccharide is from about 20 to about 50 wt. % and the polyol from about 50 to about 80 wt. % of the fluidized polymer suspension.

The other ingredient necessary in the fluidized polymer suspensions of the invention is a stabilizing agent, which will generally be present at a level of from about 0.5 to about 3 wt. % of the total weight of the suspension. The stabilizing agents are organic or inorganic materials which can be dispersed or dissolved in the polyol medium. Preferred stabilizers are silica, mineral pigments, organic pigments, crosslinked polymers and copolymers of acrylic acid, cellulose ethers and mixtures thereof. More preferred are silica and mineral pigments. Examples of mineral pigments include, but are not limited to calcium carbonate, titanium dioxide, clay, talc and gypsum. Preferred cellulose ethers for use as stabilizers are carboxymethyl cellulose and hydroxypropyl cellulose. The most preferred stabilizer is silica.

The fluidized polymers suspensions may optionally contain water. If water is used, the amount should not be so great that the suspended cationic polysaccharide swells and forms a gel. Water is generally used in an amount such that the ratio of cationic polysaccharide to water is not less than about 5:1.

For preparation of the fluidized polymer suspensions of the invention preferably the polyol is added to a high shear mixing device, and then the appropriate stabilizing agent is added. The mixture is stirred for a sufficient time to disperse the stabilizing agent, and the cationic polysaccharide is added. Further stirring is carried out until dispersion is complete. If water is utilized as a component of the fluidized polymer suspension, it can be added with the cationic polysaccharide or the stabilizing agent. However, the order of addition of the ingredients has no effect on the properties of the suspension.

The fluidized polymer suspensions of this invention find use in the formulation of personal care products, particularly hair and skin care compositions. Use of fluidized polymer suspensions of the cationic polysaccharides in place of dry powdered cationic polysaccharides has the advantages that the dusting, low rate of solution, lumping and gel formation of the powders is avoided.

Examples of personal care products of the invention include, but are not limited to shampoos, hair conditioners, combination shampoo-conditioners, sun screen products, shower gels, soaps, hair styling products, hair colorants, deodorants, antiperspirants, moisturizing lotions and the like.

The personal care products of the invention generally will comprise, in addition to the fluidized polymer suspension, some active component which provides benefit to the hair or skin. Such materials may include moisturizing agents, antiperspirants, anti-bacterials, sunscreen agents, cleaning agents, hair conditioning agents, hair styling agents, anti-dandruff agents, hair growth promoters, hair dyes and pigments, soaps and perfumes.

Typical moisturizing agents are animal oils such as lanolin and the like, fatty acid esters and fish oils; vegetable oils; mineral oils; petrolatum, and synthetic oils such as silicone oils.

A wide variety of sunscreen agents is suitable for use in the personal care compositions of the present invention. Examples include, p-aminobenzoic acid, its salts and its derivatives, anthranilates, salicylates, cinnamic acid derivatives, dihydroxy cinnamic acid derivatives, trihydroxy cinnamic acid derivatives, dibenzalacetone, dibenzalacetophenone, naphtholsulfonates, dihydroxynaphtholic acid and its salts, coumarin derivatives, diazoles, quinine salts, quinoline derivatives, hydroxy- and methoxy-substituted benzophenones, uric and vilouric acids, tannic acid and its derivatives, hydroquinone and benzophenones.

Typically, the active ingredient in deodorant-antiperspirant compositions is basic aluminum compound. Examples of such materials are aluminum chlorhydroxide, basic aluminum bromide, iodide or nitrate and basic aluminum hydroxy chloride-zirconyl hydroxy oxychloride.

Cleaning agents are typically anionic, cationic, non-ionic or amphoteric surfactants. Typical anionic surfactants are carboxylates, sulfonates, sulfates or phosphates, e.g. fatty acid soaps, salts of lauryl sulfate and salts of lauryl ether sulfate. Examples of cationic surfactants are aliphatic mono, di and polyamines derived from fatty and rosin acids, amine oxides, ethoxylated alkyl amines and imidazolines. Examples of non-ionic surfactants are polyoxyethylene surfactants, alkylphenol ethoxylates, carboxylic acid esters, e.g. mono and diglycerides, polyoxyethylene esters and fatty acid diethanolamine condensates. Amphoteric surfactants are those containing combinations of the anionic and cationic groups described above, particularly those containing both acid carboxyls and basic nitrogen groups. Typical amphoteric surfactants are imidazolines and betaines, e.g., lauric and myristic imidazolines and betaines, and amidopropylbetaines.

A wide variety of hair conditioning agents is useful in the compositions of this invention. Included are volatile hydrocarbons; silicones; cationic surfactants such as quaternary ammonium-containing cationic surfactants, e.g. di(hydrogenated tallow dimethyl ammonium chloride and cationic guar; hydrolyzed animal protein; and fatty alcohols.

Hair styling agents useful in the personal care compositions of the invention include the hair conditioning agents listed above as well as a wide variety of ionic and non-ionic polymers that are used to improve the manageability and hold of hair.

Typical soaps used as personal care active ingredients are salts of $C_8$–$C_{22}$ fatty acids.

Anti-dandruff agents, hair growth promoters and hair dyes and pigments may be any of those widely used in cosmetic formulations.

The personal care compositions of this invention comprise cationic polysaccharide thickener and some active component which provides benefit to the hair or skin. In the case of the present invention, the thickener is introduced as a fluidized polymer suspension. Both the thickener and the active ingredient are generally dissolved or suspended in a vehicle comprising water or solvent. A variety of other ingredients, in addition to those already mentioned, may be present in the vehicle. Examples of other vehicle ingredients include surfactants; colorants; antioxidants; vitamins; emulsifiers; opacifiers; pearlescent aids such as ethylene glycol distearate, or $TiO_2$ coated mica; pH modifiers such as citric acid, sodium citrate, succinic acid, phosphoric acid, sodium hydroxide and sodium carbonate; and preservatives such as benzyl alcohol, methyl paraben and propyl paraben.

The personal care compositions of this invention are readily prepared by use of conventional formulation and mixing techniques. Methods of making several personal care compositions using fluidized polymer suspensions containing cationic polysaccharides are described in the following examples, which are exemplary only and not intended to be limiting. All percentages, parts, etc., are by weight unless otherwise indicated.

EXAMPLE 1

This example describes preparation of a fluidized polymer suspension of cationic guar in polyethylene glycol.

To 55.8 parts of polyethylene glycol 400 (Dow Chemical Co., Midland, Mich.) was added 1.7 parts of Aerosil® 200 silica (Degussa AG, Hanau, Germany). The mixture was stirred with moderate shear until the silica was dispersed. Then 42.5 part of N-Hance® 3000 cationic guar (Hercules Incorporated, Wilmington, Del.) was added while the mixture was slowly stirred. A stable fluid dispersion was obtained with a viscosity of 4,500 cps (Brookfield LVT, spindle 4, 30 rpm.

The suspension was stored at ambient temperature, and the stability was checked at regular intervals. Over a period of eight weeks a small liquid layer (0–5 mm) appeared on top of the suspension. Below this layer the suspension was homogeneous.

EXAMPLE 2

This example describes preparation of a fluidized polymer suspension of cationic hydroxypropyl guar in polyethylene glycol.

The procedure described in Example 1 was followed, but using N-Hance® 3196 cationic guar (available from Hercules Incorporated, Wilmington, Del.). A stable fluid dispersion was obtained with a viscosity of 3,900 cps (Brookfield LVT, spindle 4, 30 rpm).

After storage of the dispersion for a period of two weeks at ambient temperature, a small liquid layer (0–5 mm) appeared on top of the suspension. Below this layer the suspension was homogeneous.

EXAMPLE 3

This example describes preparation of a shower gel formulation using the fluidized polymer suspension prepared in Example 1. For comparison, the same formulation was prepared using the same cationic guar, but in a dry powder form. The formulation is presented in Table 1.

TABLE 1

| INGREDIENT | PARTS PER HUNDRED |
|---|---|
| sodium laurether sulfate | 20.00 |
| disodium laurether sulfosuccinate | 20.00 |
| cocamphocarboxyglycinate | 5.00 |
| sodium lauroyl sarcosinate | 8.00 |
| propylene glycol | 2.00 |
| quat wheat | 1.00 |
| glycol distearate | 2.00 |
| fragrance | 0.35 |
| preservative | 0.60 |
| water | 40.1 |
| N-Hance ® 3000 cationic guar | 0.95 |

The cationic guar, whether as the fluidized polymer suspension or dry powder, was added as the last ingredient. When the fluidized polymer suspension was used, a sufficient amount was added to provide the level of cationic guar indicated. Hydration of the cationic guar began only after correction of the pH to about 5 by addition of citric acid. For the fluidized polymer suspension the dissolution time was 67 minutes, and no lumps were observed. For the dry powder, the dissolution time was 120 minutes, and lumps were observed.

These results indicate the substantial advantage in solution speed and lump-free dispersibility obtained with the fluidized polymer suspension.

EXAMPLE 4

This example describes preparation of a hair conditioner cream rinse formulation using the fluidized polymer suspension of Example 1. For comparison, the same formulation was prepared using the same cationic guar, but in a dry powder form. The formulation is presented in Table 2.

TABLE 2

| INGREDIENT | PARTS PER HUNDRED |
|---|---|
| glycerin | 1.00 |
| stearalkonium chloride | 3.00 |
| cetyl alcohol | 2.00 |
| fragrance | 0.30 |
| disodium EDTA | 0.10 |
| preservative | 0.40 |
| water | 92.2 |
| N-Hance ® 3000 cationic guar | 1.00 |

The cationic guar, whether as the fluidized polymer suspension or dry powder, was added as the last ingredient. When the fluidized polymer suspension was used, a sufficient amount was added to provide the level of cationic guar indicated. Hydration of the cationic guar began only after correction of the pH to about 5 by addition of citric acid. For the fluidized polymer suspension the dissolution time was 0.5 minutes, and no lumps were observed. For the dry powder, the dissolution time was 17 minutes, and lumps were observed.

These results indicate the substantial advantage in solution speed and lump-free dispersibility obtained with the fluidized polymer suspension.

EXAMPLE 5

Fluidized polymer suspensions of cationic hydroxypropyl guar (Jaguar® C-162, from Rhone-Poulenc, Paris, France), and cationic hydroxyethyl cellulose (Celquat® H-100, Celquat® L-100, Celquat® SC240-C and Celquat® SC-230-M, from National Starch and Chemical Co., Bridgewater, N.J.) were prepared using the formulation amounts and condition as described in Example 1. All of the dispersions were stable as made, but showed some thickening after storage for two weeks at room temperature.

EXAMPLE 6

This example describes preparation of a fluidized polymer suspension of cationic guar in propylene glycol.

A quantity of 14 parts of propylene glycol was added to a mixing vessel, and then 0.28 parts of carboxymethyl cellulose (CMC-7H3S from Hercules Incorporated, Wilmington, Del.) was dispersed into the propylene glycol. Then 0.02 parts of hydroxypropyl cellulose (Klucel® H from Hercules Incorporated, Wilmington, Del.) was added and dispersed with stirring. The resulting mixture was heated to 60° C. with stirring to dissolve the carboxymethyl and hydroxypropyl cellulose, and then 52.2 parts of additional propylene glycol was added. A quantity of 30 parts of cationic guar was added to the solution with stirring to complete the procedure.

The product was a pourable fluidized polymer suspension of cationic guar in propylene glycol that showed no sign of separation after standing overnight at room temperature.

It is not intended that the examples presented here should be construed to limit the invention, but rather they are submitted to illustrate some specific embodiments of the invention. Various modifications and variations of the present invention can be made without departing from the scope of the appended claims.

What is claimed is:

1. A fluidized polymer suspension comprising:
   a) cationic polysaccharide at a level of from about 10 to about 65 wt. % of the total fluidized polymer suspension,
   b) stabilizing agent selected from the group consisting of silica, mineral pigments, organic pigments, crosslinked polymers and copolymers of acrylic acid, cellulose ethers and mixtures thereof at a level of from about 0.5 to about 3 wt. % of the fluidized polymer suspension, and
   c) water-soluble polyol that is a non-solvent for the cationic polysaccharide at a level of from about 35 to about 90 wt.% of the fluidized polymer suspension,
       wherein the fluidized polymer suspension is a liquid suspension of particulate cationic polysaccharide in the water soluble polyol, and is stable against agglomeration for at least one week.

2. The fluidized polymer suspension of claim 1 wherein the suspension is stable for at least about 8 weeks.

3. The fluidized polymer suspension of claim 1 wherein the suspension is stable for at least about 6 months.

4. The fluidized polymer suspension of claim 1 wherein the cationic polysaccharide is at least one member selected from the group consisting of cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose.

5. The fluidized polymer suspension of claim 1 wherein the cationic polysaccharide comprises cationic guar.

6. The fluidized polymer suspension of claim 1 wherein the cationic polysaccharide comprises cationic hydroxypropyl guar.

7. The fluidized polymer suspension of claim 1 wherein the water-soluble polyol that is a non-solvent for the cationic polysaccharide is selecred from the group consisting of polyethylene glycol, polypropylene glycol, diethylene glycol, glycerine, propylene glycol, ethylene glycol and mixtures thereof.

8. The fluidized polymer suspension of claim 1 wherein the water-soluble polyol that is a non-solvent for the cationic polysaccharide comprises polyethylene glycol having a molecular weight between about 150 and 600.

9. The fluidized polymer suspension of claim 1 wherein the stabilizing agent comprises mineral pigment selected from the group consisting of calcium carbonate, titanium dioxide, clay, talc, and gypsum.

10. The fluidized polymer suspension of claim 1 wherein the stabilizing agent comprises silica.

11. The fluidized polymer suspension of claim 1 wherein the cationic polysaccharide is from about 15 to about 60 wt. % of the total weight of the fluidized polymer suspension.

12. The fluidized polymer suspension of claim 1 wherein the cationic polysaccharide is from about 20 to about 50 wt. % of the total weight of the fluidized polymer suspension.

13. The fluidized polymer suspension of claim 1 wherein the water-soluble polyol that is a non-solvent for the cationic polysaccharide is from about 50 to about 80 wt. % of the total weight of the fluidized polymer suspension.

14. The fluidized polymer suspension of claim 1 further comprising water.

15. The fluidized polymer suspension of claim 1 wherein the cationic polysaccharide is at least one member selected from the group consisting of cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose, and
    the water-soluble polyol that is a non-solvent for the cationic polysaccharide is selected from the group consisting of polyethylene glycol, polypropylene glycol, diethylene glycol, glycerine, propylene glycol, ethylene glycol and mixtures thereof.

16. The fluidized polymer suspension of claim 1 wherein the cationic polysaccharide comprises cationic guar, the water-soluble polyol that is a non-solvent for the cationic polysaccharide comprises polyethylene glycol having a molecular weight between about 150 and 600, and the stabilizing agent comprises silica.

17. The fluidized polymer suspension of claim 1 wherein the cationic polysaccharide comprises cationic hydroxypropyl guar, the water-soluble polyol that is a non-solvent for the cationic polysaccharide comprises polyethylene glycol having a molecular weight between about 150 and 600, and the stabilizing agent comprises silica.

* * * * *